United States Patent
Tanaka (10) Patent No.: US 8,167,792 B2
(45) Date of Patent: May 1, 2012

(54) ENDOSCOPE SYSTEM HAVING PASSAGE POSITION SETTING SECTION AND PASSAGE POSITION CORRECTION SECTION

(75) Inventor: Hideki Tanaka, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 99 days.

(21) Appl. No.: 12/783,040

(22) Filed: May 19, 2010

(65) Prior Publication Data

US 2010/0283841 A1    Nov. 11, 2010

Related U.S. Application Data

(63) Continuation of application No. PCT/JP2009/067554, filed on Oct. 8, 2009.

(30) Foreign Application Priority Data

Jan. 29, 2009    (JP) ................................ 2009-018485

(51) Int. Cl.
    *A61B 1/04* (2006.01)
(52) U.S. Cl. ......... 600/117; 600/103; 600/109; 600/118
(58) Field of Classification Search ................. 600/117, 600/118, 109, 921, 103; 348/65; 382/128
    See application file for complete search history.

(56) References Cited

U.S. PATENT DOCUMENTS

| | | | | |
|---|---|---|---|---|
| 4,910,590 A * | 3/1990 | Gillies et al. | ..................... | 348/65 |
| 4,916,533 A * | 4/1990 | Gillies et al. | ..................... | 348/65 |
| 5,018,509 A * | 5/1991 | Suzuki et al. | ................. | 600/115 |
| 5,036,464 A | 7/1991 | Gillies et al. | | |
| 5,347,987 A * | 9/1994 | Feldstein et al. | .............. | 600/109 |
| 5,469,254 A * | 11/1995 | Konomura | ................. | 356/241.1 |
| 5,469,840 A * | 11/1995 | Tanii et al. | ..................... | 600/117 |
| 5,658,238 A | 8/1997 | Suzuki et al. | | |
| 7,258,664 B2 * | 8/2007 | Nishimura et al. | ........... | 600/117 |
| 7,559,888 B2 * | 7/2009 | Hasegawa et al. | ........... | 600/117 |
| 7,811,226 B2 * | 10/2010 | Nishimura et al. | ........... | 600/117 |
| 7,854,699 B2 * | 12/2010 | Nishimura et al. | ........... | 600/117 |
| 7,857,752 B2 * | 12/2010 | Hasegawa et al. | ........... | 600/109 |
| 7,878,971 B2 * | 2/2011 | Nishimura et al. | ........... | 600/117 |

(Continued)

FOREIGN PATENT DOCUMENTS

EP    2 008 571 A1    12/2008

(Continued)

OTHER PUBLICATIONS

International Search Report dated Dec. 8, 2009.

*Primary Examiner* — John P Leubecker
(74) *Attorney, Agent, or Firm* — Scully, Scott, Murphy & Presser, P.C.

(57) ABSTRACT

An endoscope system includes an endoscope provided with an image pickup section that picks up an image of an object in a body cavity, a position setting section that sets information on a predetermined position in the object based on information obtained from the image of the object picked up by the image pickup section and a position correction section that corrects the information on the predetermined position set by the position setting section based on information on a boundary line extracted in the image of the object picked up by the image pickup section and outputs information on the corrected position.

7 Claims, 8 Drawing Sheets

U.S. PATENT DOCUMENTS

| | | |
|---|---|---|
| 7,905,829 B2 * | 3/2011 | Nishimura et al. ............ 600/117 |
| 8,038,605 B2 * | 10/2011 | Tsuji et al. .................... 600/152 |
| 2003/0069474 A1 | 4/2003 | Couvillon, Jr. |
| 2003/0069475 A1 | 4/2003 | Banik et al. |
| 2005/0065400 A1 | 3/2005 | Banik et al. |
| 2005/0107669 A1 | 5/2005 | Couvillon, Jr. |
| 2006/0293563 A1 | 12/2006 | Banik et al. |
| 2009/0041320 A1 | 2/2009 | Tanaka |

FOREIGN PATENT DOCUMENTS

| | | |
|---|---|---|
| GB | 2 238 440 A | 5/1991 |
| JP | 03-165732 | 7/1991 |
| JP | 05-228102 | 9/1993 |
| JP | 07-155289 | 6/1995 |
| JP | 2005-527253 | 9/2005 |
| JP | 2005-530556 | 10/2005 |
| JP | 2007-282857 | 11/2007 |
| WO | WO 03/030727 A2 | 4/2003 |
| WO | WO 04/000107 A2 | 12/2003 |
| WO | WO 2007/119296 A1 | 10/2007 |

* cited by examiner

ENDOSCOPE SYSTEM HAVING PASSAGE POSITION SETTING SECTION AND PASSAGE POSITION CORRECTION SECTION

CROSS REFERENCE TO RELATED APPLICATION

This application is a continuation application of PCT/JP2009/067554 filed on Oct. 8, 2009 and claims benefit of Japanese Application No. 2009-018485 filed in Japan on Jan. 29, 2009, the entire contents of which are incorporated herein by this reference.

BACKGROUND OF THE INVENTION

1. Field of the Invention

The present invention relates to an endoscope system, and more particularly, to an endoscope system capable of supporting insertion of an endoscope into an object to be examined such as a body cavity.

2. Description of the Related Art

Endoscopes are conventionally widely used in the medical field and industrial field or the like, and, for example, in the medical field, endoscopes are used to perform observation and various kinds of treatment on living tissue or the like in the body cavity.

Furthermore, Japanese Patent Application Laid-Open Publication No. 7-155289 discloses a technique of setting a target position (moving direction and amount of movement) as appropriate when extracting a dark region in an observed image obtained by an endoscope and inserting the endoscope in such a way that the center position of the dark region matches the center position of the observed image.

SUMMARY OF THE INVENTION

An endoscope system according to the present invention includes an endoscope provided with an image pickup section that picks up an image of an object in a body cavity, a position setting section that sets information on a predetermined position in the object based on information obtained from the image of the object picked up by the image pickup section and a position correction section that corrects the information on the predetermined position set by the position setting section based on information on a boundary line extracted in the image of the object picked up by the image pickup section and outputs information on the corrected position.

DETAILED DESCRIPTION OF THE PREFERRED EMBODIMENT

Hereinafter, an embodiment of the present invention will be described with reference to the accompanying drawings.

Figure 1:
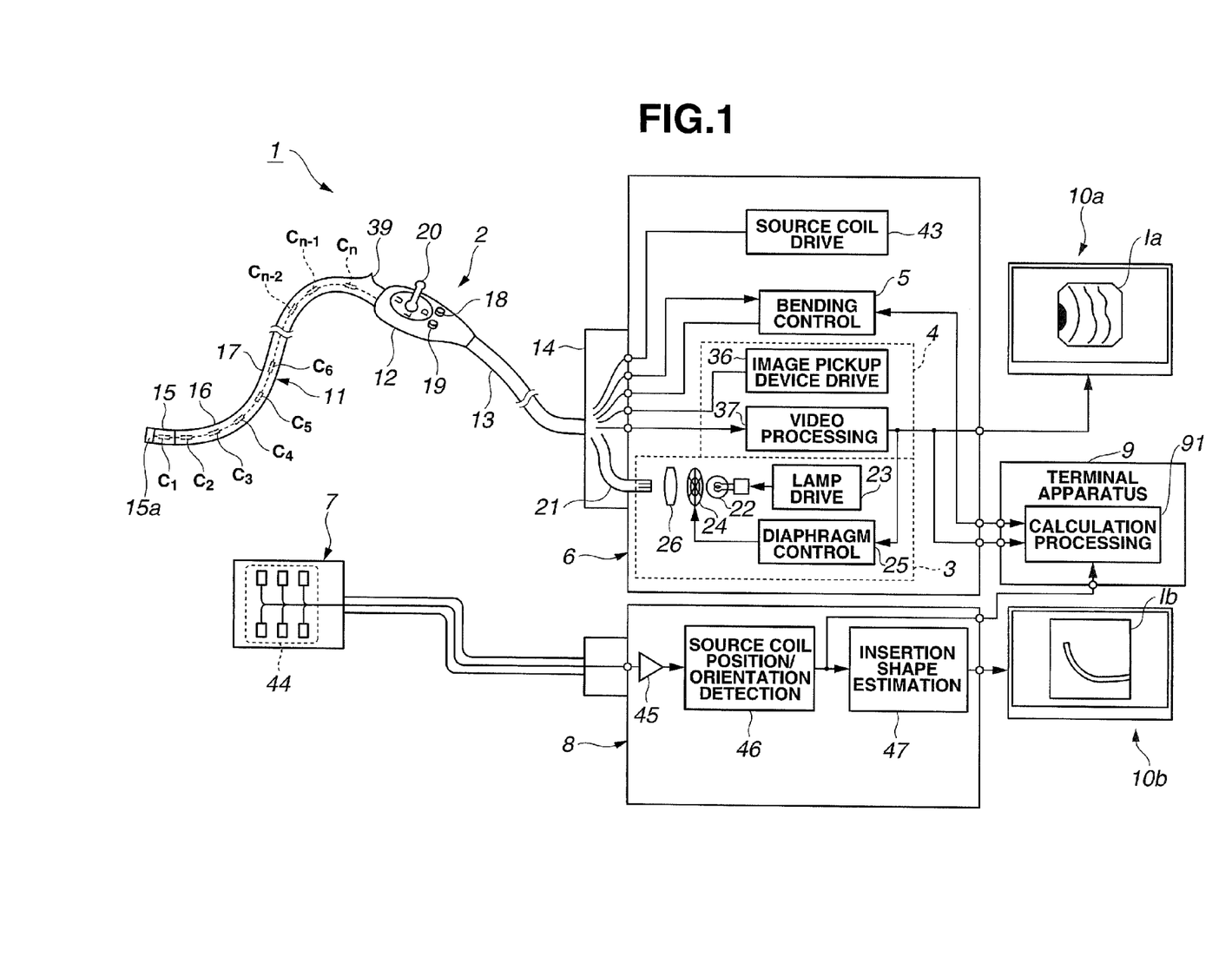
FIG. 1 is a diagram illustrating an example of a configuration of main parts of an endoscope system according to an embodiment of the present invention.
Figure 2:
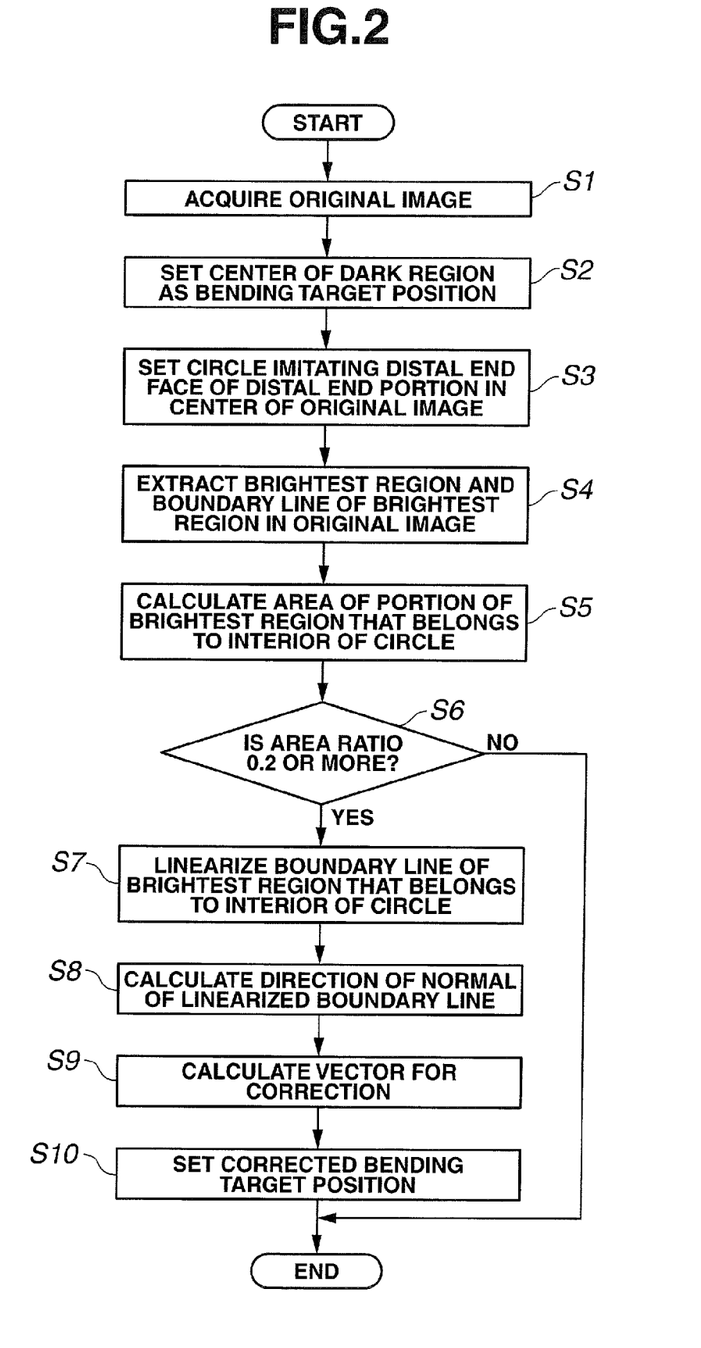
FIG. 2 is a diagram illustrating an example of processing performed to set a bending target position.
Figure 3:
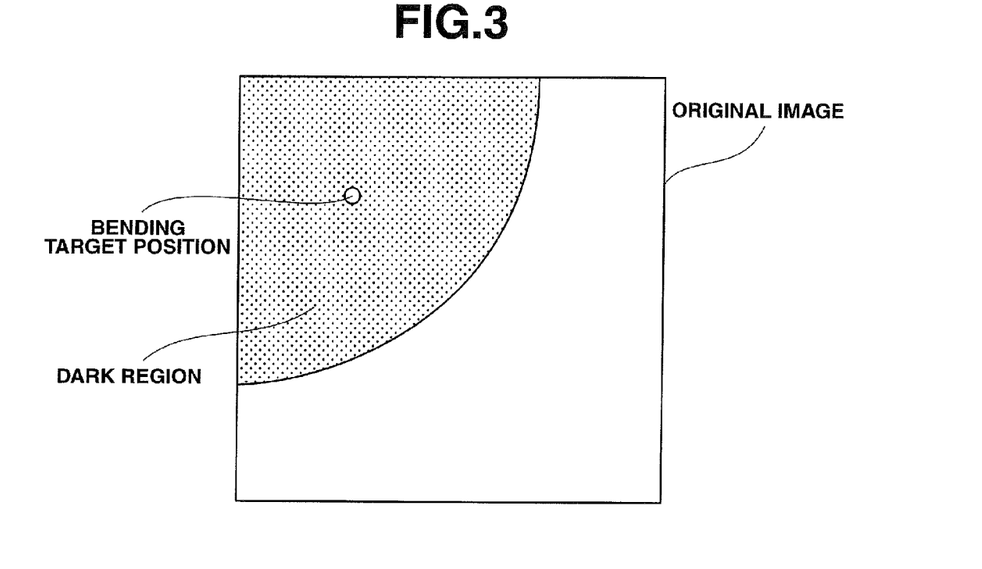
FIG. 3 is a diagram illustrating an example of a bending target position in an original image.
Figure 4:
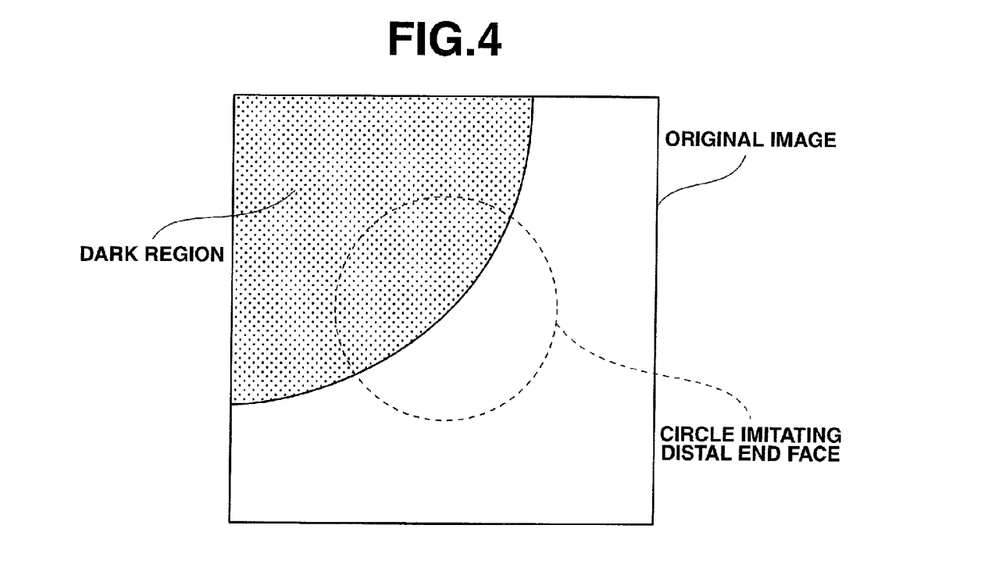
FIG. 4 is a diagram illustrating an example where a circle imitating the distal end face of the distal end portion of the endoscope is set in an original image.
Figure 5:
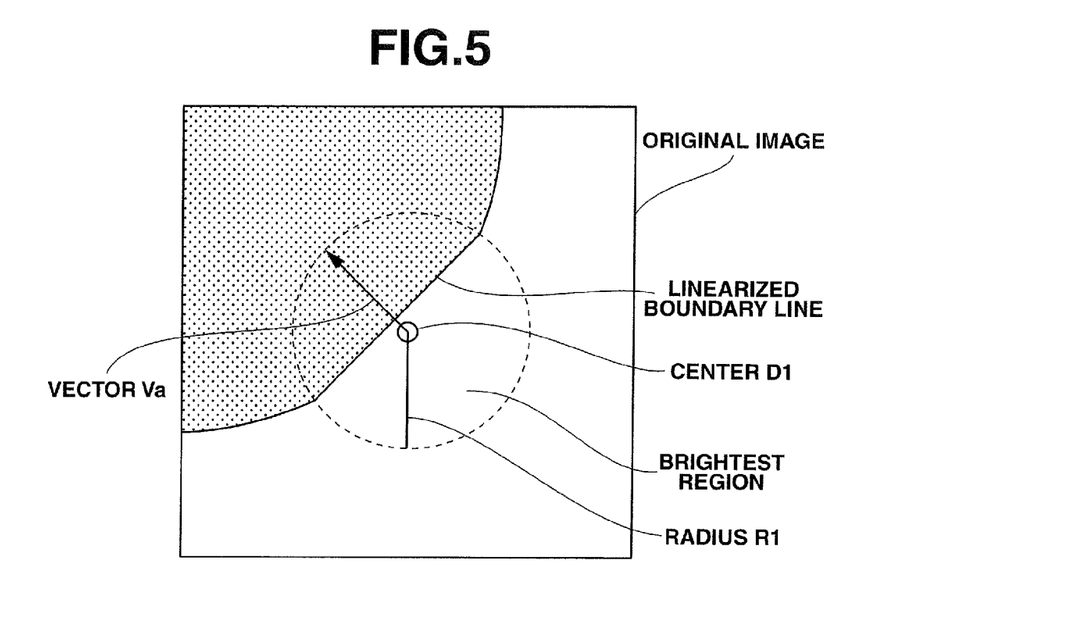
FIG. 5 is a diagram illustrating an example of a vector for correcting the bending target position.
Figure 6:
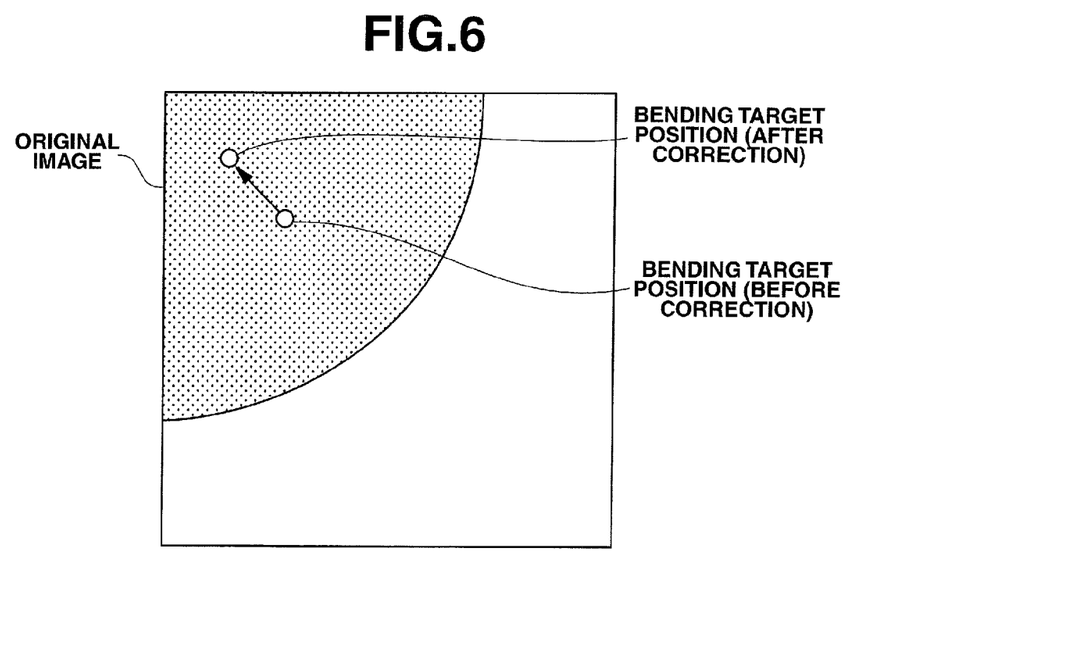
FIG. 6 is a diagram illustrating an example where the bending target position in FIG. 3 is corrected to a new bending target position.
Figure 7:
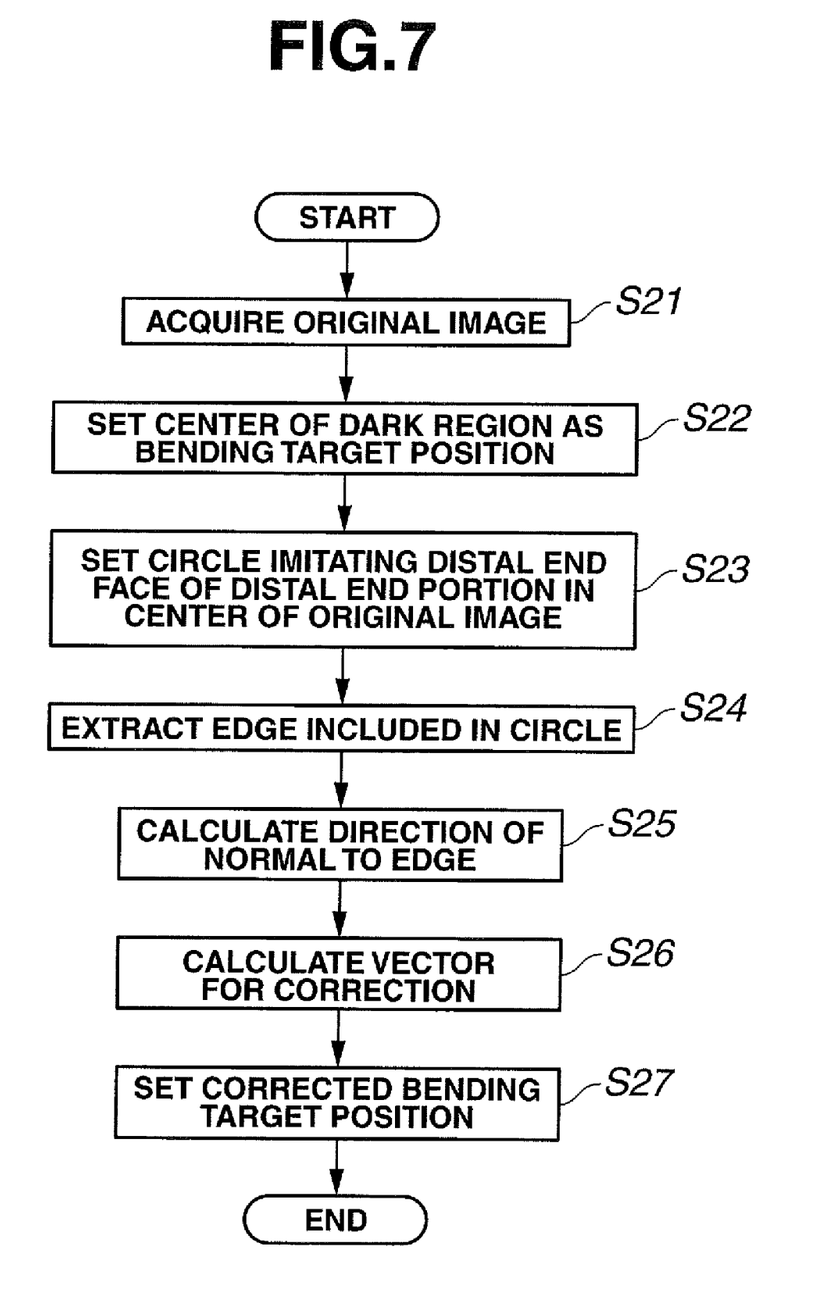
FIG. 7 is a diagram illustrating a first modification example of the processing performed to set a bending target position.
Figure 8:
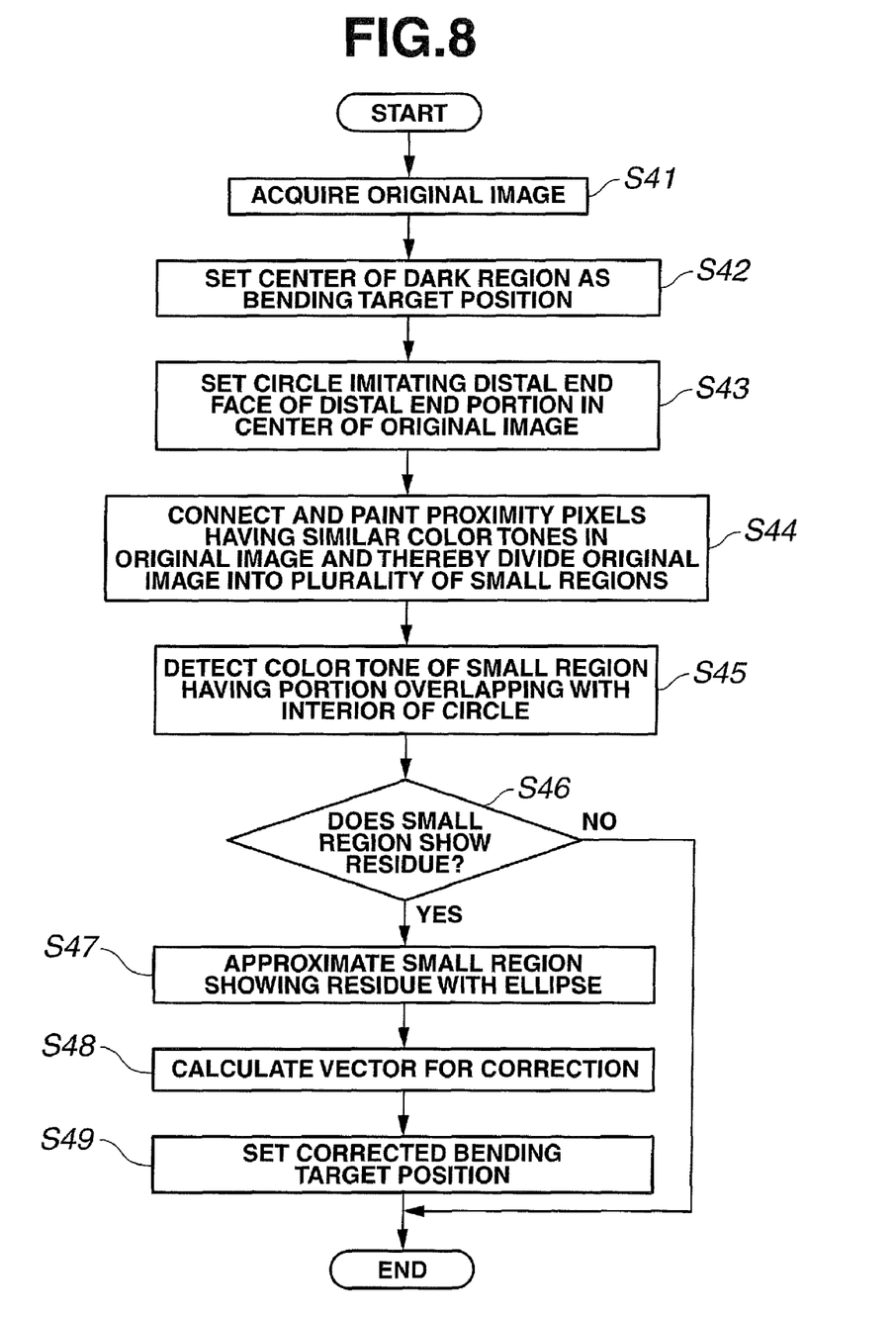
FIG. 8 is a diagram illustrating a second modification example of the processing performed to set a bending target position.
Figure 9:
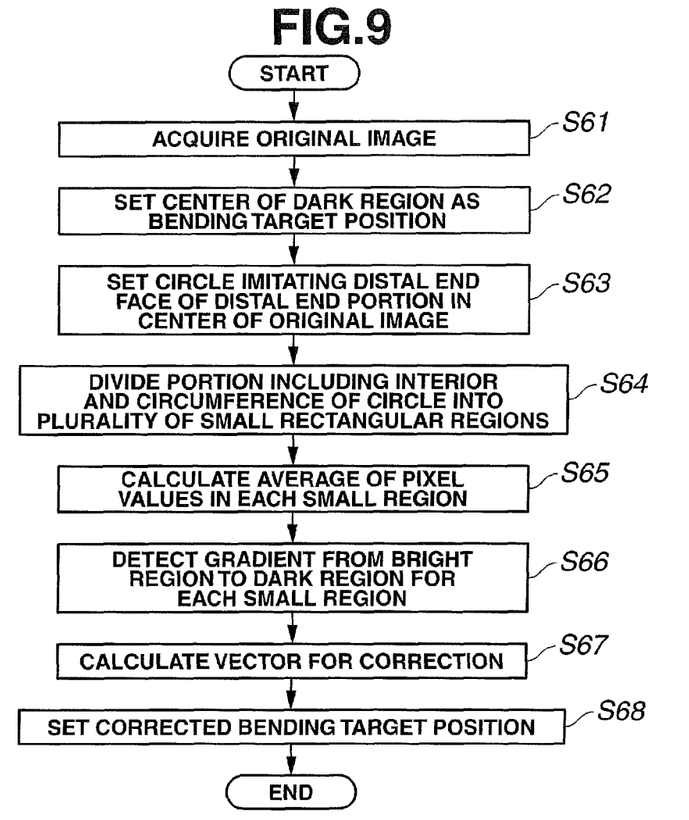
FIG. 9 is a diagram illustrating a third modification example of the processing performed to set a bending target position.
Figure 10:
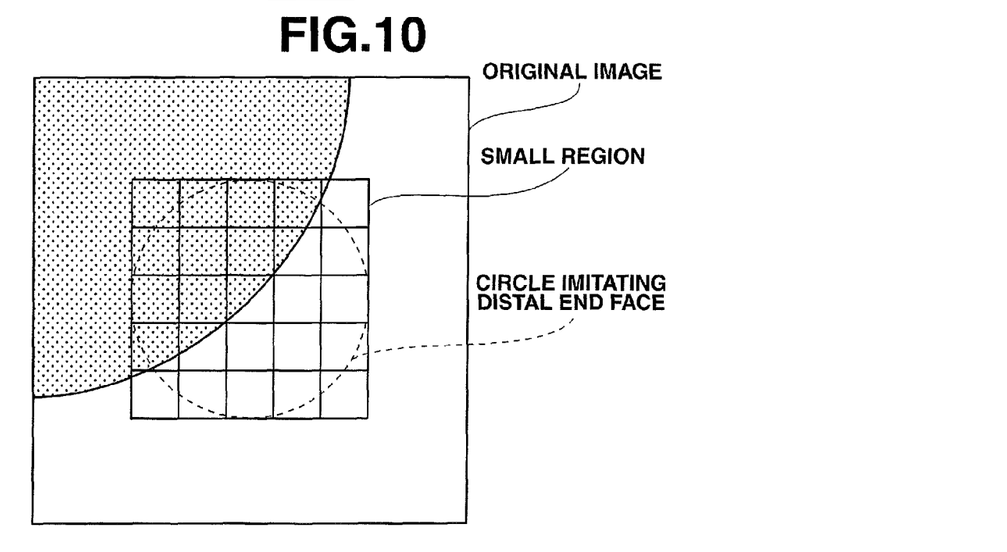
FIG. 10 is a diagram illustrating an example where a circle imitating the distal end face of the distal end portion of the endoscope is set in an original image and a portion including the interior and boundary of the circle is divided into a plurality of small regions.
Figure 11:
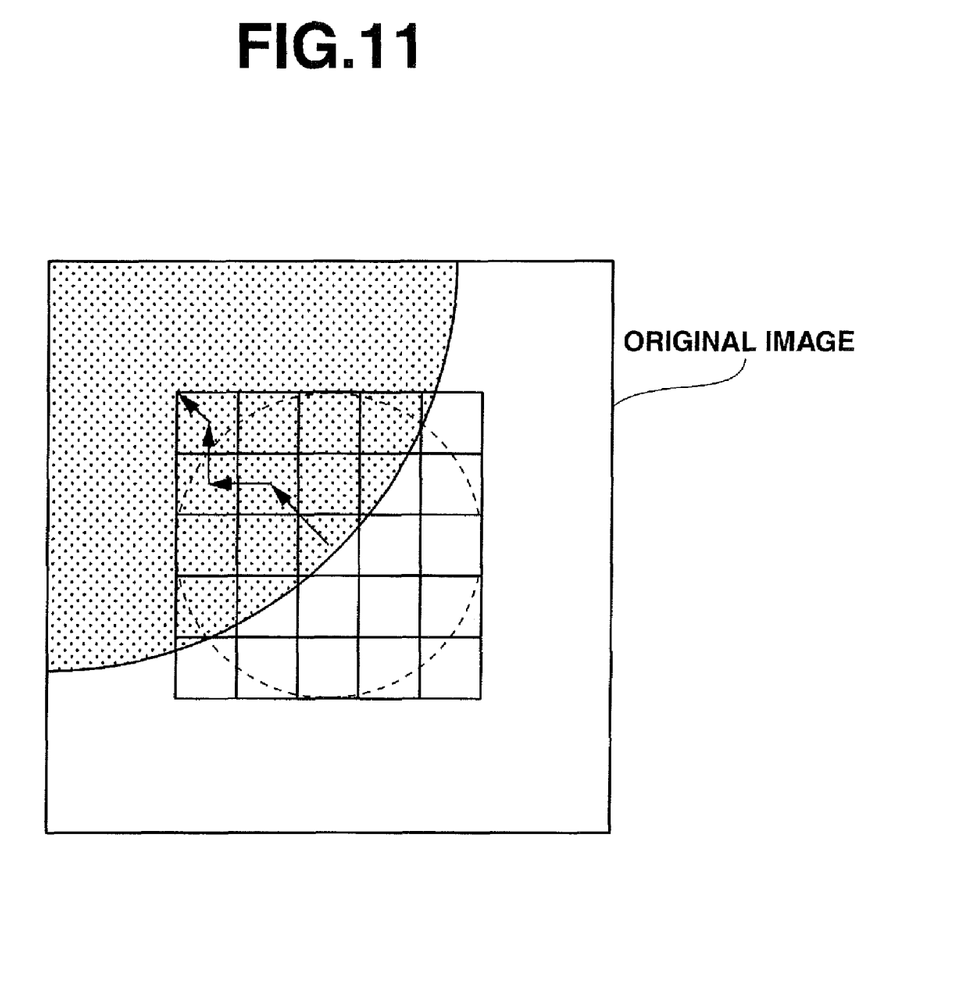
FIG. 11 is a diagram illustrating an example of a route acquired when a gradient direction from a bright region toward a dark region is sequentially traced.

FIG. 1 to FIG. 11 are related to the embodiment of the present invention. FIG. 1 is a diagram illustrating an example of a configuration of main parts of an endoscope system according to an embodiment of the present invention. FIG. 2 is a diagram illustrating an example of processing performed to set a bending target position. FIG. 3 is a diagram illustrating an example of a bending target position in an original image. FIG. 4 is a diagram illustrating an example where a circle imitating the distal end face of the distal end portion of the endoscope is set in an original image. FIG. 5 is a diagram illustrating a vector for correcting the bending target position obtained in the processing in FIG. 2. FIG. 6 is a diagram illustrating an example where the bending target position in FIG. 3 is corrected to a new bending target position. FIG. 7 is a diagram illustrating a first modification example of the processing performed to set a bending target position. FIG. 8 is a diagram illustrating a second modification example of the processing performed to set a bending target position. FIG. 9 is a diagram illustrating a third modification example of the processing performed to set a bending target position. FIG. 10 is a diagram illustrating an example where a circle imitating the distal end face of the distal end portion of the endoscope is set in an original image and a portion including the interior and boundary of the circle is divided into a plurality of small regions. FIG. 11 is a diagram illustrating an example of a route acquired when a gradient direction from a bright region toward a dark region is sequentially traced.

As shown in FIG. 1, an endoscope system 1 is configured by including an endoscope 2 inserted into a body cavity of a patient as an object to be examined to pick up an image of the object in the body cavity, a processor 6 to/from which a connector 14 provided in the endoscope 2 can be attached/detached, a sense coil unit 7 disposed in a periphery of a bed on which the patient lies, an endoscope insertion shape detection apparatus 8, a terminal apparatus 9 and monitors 10a and 10b.

Furthermore, the processor 6 includes a light source section 3 that supplies illumination light for illuminating an object which becomes an image pickup target to the endoscope 2, a signal processing section 4 that performs signal processing on an image pickup signal outputted from the endoscope 2 and thereby generates and outputs a video signal, a bending control section 5 that performs bending control on the endoscope 2 and a source coil drive section 43.

The endoscope 2 includes an elongated insertion portion 11 inserted into the body cavity of the object to be examined, an operation section 12 provided at a rear end of the insertion portion 11 and a universal cord 13 that extends out from the operation section 12. The connector 14 attachable/detachable to/from the processor 6 is provided at a rear end of the universal cord 13.

The insertion portion 11 includes a rigid distal end portion 15 provided at a distal end, a bending portion 16 connected at a rear end of the distal end portion 15 and a flexible tube portion 17 having flexibility provided between a rear end of the bending portion 16 and a front end of the operation section 12. Furthermore, n source coils C1, C2, ..., Cn that generate magnetic fields corresponding to a source coil drive signal applied from the source coil drive section 43 are provided at substantially equal intervals inside the insertion portion 11.

The distal end portion 15 is configured by including a circular distal end face. Furthermore, an image pickup section 15a provided with an objective optical system that forms an image of an object and an image pickup device that outputs the image of the object formed through the objective optical system as an image pickup signal or the like is provided at the distal end portion 15.

The operation section 12 is provided with a scope switch 18 that instructs acquisition of a freeze image (still image) or the like, a bending mode changeover switch 19 that instructs changeover of the bending mode of the bending portion 16 to a manual mode or an automatic mode and a bending joystick 20 that instructs, when the manual mode is selected, a bending direction and a bending angle of the bending portion 16. Furthermore, a treatment instrument insertion port 39 through which a treatment instrument or the like can be inserted and which leads to a channel (not shown) for the treatment instrument is provided at a portion on the rear end side of the flexible tube portion 17 and near the front end of the operation section 12.

A light guide 21 that transmits illumination light supplied from the light source section 3 to the distal end portion 15 is inserted into the insertion portion 11 or the like of the endoscope 2.

One end face (incident end face) of the light guide 21 is disposed protruding from the connector 14. On the other hand, the other end face (outgoing end face) of the light guide 21 is disposed in the vicinity of an illumination optical system (not shown) provided at the distal end portion 15. In such a configuration, when the connector 14 is connected to the processor 6, the illumination light supplied from the light source section 3 passes through the light guide 21 and an illumination optical system (not shown) and illuminates the object which is the image pickup target of the image pickup section 15a.

The light source section 3 provided with the function as a light source apparatus includes a lamp 22 that emits illumination light which is, for example, white color light, a lamp drive section 23 that supplies power necessary to drive the lamp 22, a diaphragm 24, a diaphragm control section 25 that increases/decreases the amount of diaphragm (amount of aperture) of the diaphragm 24 based on a video signal outputted from the signal processing section 4 and a condensing optical system 26 that supplies the illumination light to the incident end face of the light guide 21 while condensing the illumination light that has passed through the diaphragm 24.

The diaphragm control section 25 calculates average brightness based on, for example, the luminance component of a video signal inputted, increases/decreases the amount of diaphragm (amount of aperture) of the diaphragm 24 based on a difference value which is a value obtained by subtracting a reference value corresponding to appropriate brightness from the average brightness and thereby changes the light amount of the illumination light that passes through the diaphragm 24 as appropriate.

The signal processing section 4 includes an image pickup device drive section 36 that outputs an image pickup device drive signal to drive an image pickup device provided in the image pickup section 15a and a video processing section 37 that generates and outputs a video signal by applying signal processing to the image pickup signal outputted from the image pickup section 15a. In this way, the monitor 10a displays an endoscope image Ia corresponding to the video signal.

When the bending mode of the bending portion 16 is changed to a manual mode based on an instruction given by the bending mode changeover switch 19, the bending control section 5 performs control to change the direction of bending and the angle of bending of the bending portion 16 based on the direction of inclination and the amount of inclination of the bending joystick 20. Furthermore, when the bending mode of the bending portion 16 is changed to an automatic mode based on an instruction given by the bending mode changeover switch 19, the bending control section 5 performs control to change the direction of bending and the angle of bending of the bending portion 16 based on the calculation result of the terminal apparatus 9.

The source coil drive section 43 is connected to the n source coils C1, C2, ..., Cn provided inside the insertion portion 11 and sequentially applies AC source coil drive signals to the respective source coils. Thus, an AC magnetic field is generated around each source coil provided inside the insertion portion 11.

The sense coil unit 7 is provided with a sense coil group 44 that detects magnetic fields emitted from the n source coils C1, C2, ..., Cn provided inside the insertion portion 11 and outputs the detected values as magnetic field detection signals.

The endoscope insertion shape detection apparatus 8 includes an amplifier 45 that amplifies the magnetic field detection signals outputted from the sense coil unit 7, a source coil position/orientation detection section 46 that detects three-dimensional coordinate positions and orientations of the n source coils C1, C2, ..., Cn based on the magnetic field detection signals outputted from the amplifier 45 and outputs the detected values as insertion shape information and an insertion shape estimation section 47 that estimates an insertion shape of the insertion portion 11 based on the insertion shape information outputted from the source coil position/orientation detection section 46 and outputs the estimated value as an insertion shape image signal. In this way, the monitor 10b displays an insertion shape image Ib of the insertion portion 11 corresponding to the insertion shape image signal.

The terminal apparatus 9 includes a calculation processing section 91 that carries out a calculation on bending control performed when the bending mode of the bending portion 16 is an automatic mode based on the video signal outputted from the video processing section 37 and the insertion shape information outputted from the source coil position/orientation detection section 46 and outputs the calculation result to the bending control section 5. More specific contents of the calculation performed by the calculation processing section 91 will be described later.

Furthermore, the terminal apparatus 9 is provided with a memory (not shown) that can temporarily store the calculation result or the like of the calculation processing section 91.

Next, operations of the endoscope system 1 will be described. Hereinafter, suppose descriptions of the control when the bending mode changeover switch 19 is changed to the manual bending mode will be omitted and descriptions will be focused on the control when the bending mode changeover switch 19 is changed to the automatic bending mode.

The operator connects and starts each section of the endoscope system 1 first, and then inserts the insertion portion 11 of the endoscope 2 into the body cavity of the patient and changes the bending mode changeover switch 19 to the automatic bending mode. Accordingly, image pickup of the object by the image pickup section 15a of the endoscope 2 starts and each source coil provided in the insertion portion 11 starts to generate a magnetic field.

An image pickup signal outputted from the image pickup section 15a along with image pickup of the object is outputted to the processor 6 through the universal cord 13 and the connector 14, converted to a video signal by the video processing section 37 and then inputted to the calculation processing section 91 of the terminal apparatus 9. On the other hand, a magnetic field detection signal outputted from the sense coil unit 7 along with generation of the magnetic field in each source coil provided in the insertion portion 11 is amplified by the amplifier 45, converted as three-dimensional coordinate information of the source coil by the source coil position/orientation detection section 46, an insertion shape thereof is estimated by the insertion shape estimation section 47, and then inputted to the calculation processing section 91 of the terminal apparatus 9 as an insertion shape image signal.

The calculation processing section 91 of the terminal apparatus 9 performs processing based on the inputted video signal and insertion shape image signal or the like, thereby sets a bending target position (passage target position) which becomes a passage target of the distal end portion 15 and outputs information on the set bending target position to the bending control section 5.

Here, the processing performed by the calculation processing section 91 when setting the aforementioned bending target position will be described.

First, the calculation processing section 91 acquires an original image corresponding to an inputted video signal (step S1 in FIG. 2).

Next, the calculation processing section 91 provided with the function as a position setting section extracts a dark region in the original image acquired in step S1 in FIG. 2 and then sets the center of the dark region as a bending target position (passage target position of the distal end portion 15) of the bending portion 16 by using publicly known processing (step S2 in FIG. 2). Through such processing, a pixel position in the original image as shown, for example, in FIG. 3 is set as a bending target position.

Furthermore, the calculation processing section 91 sets a circle imitating the distal end face of the distal end portion 15 in the center of the acquired original image (step S3 in FIG. 2) and then extracts the brightest region and a boundary line of the brightest region in the original image (step S4 in FIG. 2). The circle imitating the distal end face of the distal end portion 15 is as shown, for example, in FIG. 4.

Here, a more specific example of the processing performed to extract the brightest region will be described.

First, the calculation processing section 91 divides the original image into a plurality of equally spaced rectangular regions, identifies one pixel corresponding to the center of gravity of the rectangular region having the highest average of pixel values, and then compares pixel values of four nearby pixels neighboring the one pixel with a predetermined threshold.

Next, while regarding pixels provided with pixel values equal to or above the predetermined threshold as pixels that belong to the brightest region, the calculation processing section 91 compares pixel values of four neighboring pixels of each pixel which has newly come to belong to the brightest region with a predetermined threshold.

By repeatedly performing the aforementioned comparison processing until no pixel regarded as belonging to the brightest region is left, it is possible to obtain extraction results of the brightest region and the boundary line of the brightest region.

On the other hand, the calculation processing section 91 calculates the area of the portion of the brightest region extracted in step S4 in FIG. 2 that belongs to the interior of the circle set in step S3 in FIG. 2 (step S5 in FIG. 2).

After that, the calculation processing section 91 judges whether the ratio of the area of the brightest region inside the circle to the area of the entire circle set in step S3 in FIG. 2 is 0.2 or more (step S6 in FIG. 2). Upon detecting that the area ratio is less than 0.2, the calculation processing section 91 considers it unnecessary to correct the bending target position calculated in step S2 in FIG. 2 and outputs the calculation result of the bending target position to the bending control section 5. Furthermore, upon detecting that the area ratio is 0.2 or above, the calculation processing section 91 considers it necessary to correct the bending target position calculated in step S2 in FIG. 2 and continues to perform processing from step S7 in FIG. 2 onward.

The calculation processing section 91 performs processing such as a Hough transform and thereby linearizes the boundary line in the brightest region that belongs to the interior of the circle set in step S3 in FIG. 2 (step S7 in FIG. 2).

Furthermore, the calculation processing section 91 calculates the direction of the normal to the boundary line linearized in step S7 in FIG. 2 (step S8 in FIG. 2). To be more specific, the calculation processing section 91 calculates a direction opposite to the direction in which the center of gravity of the brightest region that belongs to the interior of the circle exists as the direction of the normal to the boundary line linearized in step S7 in FIG. 2.

Next, the calculation processing section 91 calculates a vector for correcting the bending target position Va having a center D1 of the circle set in step S3 in FIG. 2 as a starting point, having the same size as a radius R1 of the circle and oriented toward the same direction as the direction of the normal calculated in step S8 in FIG. 2 as a vector as shown, for example, in FIG. 5 (step S9 in FIG. 2). Furthermore, before and after the processing in step S9 in FIG. 2, the calculation processing section 91 performs processing of calculating a vector Vb, the starting point of which is the center D1 of the circle set in step S3 in FIG. 2 and the end point of which is the bending target position calculated in step S2 in FIG. 2.

The calculation processing section 91 provided with the function as a position correction section generates a combined vector obtained by adding up the aforementioned vectors Va and Vb at a first ratio and then sets the pixel position which corresponds to the end point of the combined vector as the corrected bending target position (step S10 in FIG. 2). Through such processing, the bending target position calculated in step S2 in FIG. 2 is corrected to a new bending target position as shown, for example, in FIG. 6.

After that, the calculation processing section 91 outputs the calculation result of the corrected bending target position obtained in step S10 in FIG. 2 to the bending control section 5.

The bending control section 5 then performs control based on the processing result of the series of processes shown in FIG. 2, and can thereby bend the bending portion 16 so as to avoid contact of the distal end face of the distal end portion 15 with the fold or body wall in the body cavity as much as possible.

According to the present embodiment, as shown, for example, in the following modification examples, it is also possible to correct the bending target position using the extraction result of the dark region in the original image and elements other than the extraction result of the brightest region in the original image.

Here, as a first modification example of the present embodiment, a series of processes performed to correct the bending target position using an extraction result of a dark region in an original image and an extraction result of an edge in the original image will be described with reference to FIG. 7.

First, the calculation processing section 91 acquires an original image corresponding to an inputted video signal (step S21 FIG. 7).

Next, the calculation processing section 91 extracts a dark region in the original image acquired in step S21 in FIG. 7, and then sets the center of the dark region as a bending target position of the bending portion 16 (passage target position of the distal end portion 15) using publicly known processing (step S22 in FIG. 7).

Furthermore, the calculation processing section 91 sets a circle imitating the distal end face of the distal end portion 15 in the center of the acquired original image (step S23 in FIG. 7) and then extracts an edge included in the circle (step S24 in FIG. 7).

After that, the calculation processing section 91 calculates the direction of the normal to the edge extracted in step S24 in FIG. 7 (step S25 in FIG. 7). To be more specific, the calculation processing section 91 calculates such a direction that the angle formed with a vector oriented from the center of the edge toward the bending target position is less than 90° as the direction of the normal of the edge.

Next, the calculation processing section 91 calculates a vector for correcting the bending target position Vc having a center D2 of the circle set in step S23 in FIG. 7 as a starting point, having the same size as the radius R2 of the circle and oriented in the same direction as the direction of the normal calculated in step S25 in FIG. 7 (step S26 in FIG. 7). Furthermore, before and after the processing in step S26 in FIG. 7, the calculation processing section 91 performs processing of calculating a vector Vd, the starting point of which is the center D2 of the circle set in step S23 in FIG. 7 and the end point of which is the bending target position calculated in step S22 in FIG. 7.

The calculation processing section 91 generates a combined vector obtained by adding up the aforementioned vectors Vc and Vd at a second ratio and then sets a pixel position which corresponds to the end point of the combined vector as the corrected bending target position (step S27 in FIG. 7). Through such processing, the bending target position calculated in step S22 in FIG. 7 is corrected to a new bending target position.

After that, the calculation processing section 91 outputs the calculation result of the corrected bending target position obtained in step S27 in FIG. 7 to the bending control section 5.

The bending control section 5 then performs control based on the processing result of the series of processes shown in FIG. 7, and can thereby bend the bending portion 16 so as to avoid contact of the distal end face of the distal end portion 15 with the fold or body wall in the body cavity as much as possible.

Here, as a second modification example of the present embodiment, a series of processes performed to correct the bending target position using the extraction result of the dark region in the original image and the extraction result of color tone in the original image will be described with reference to FIG. 8.

First, the calculation processing section 91 acquires an original image corresponding to an inputted video signal (step S41 in FIG. 8).

Next, the calculation processing section 91 extracts a dark region in the original image acquired in step S41 in FIG. 8 and then sets the center of the dark region as a bending target position of the bending portion 16 (passage target position of the distal end portion 15) using publicly known processing (step S42 in FIG. 8).

Furthermore, the calculation processing section 91 sets a circle imitating the distal end face of the distal end portion 15 in the center of the acquired original image (step S43 in FIG. 8), then connects and paints proximity pixels having similar color tones in the original image and thereby divides the original image into a plurality of small regions (step S44 in FIG. 8). Suppose the calculation processing section 91 performs processing using a watershed algorithm or segmentation algorithm based on an image pyramid or the like as the processing in step S44 in FIG. 8.

The calculation processing section 91 detects a color tone of a small region having a portion overlapping with the interior of the circle set in step S43 in FIG. 8 out of the plurality of small regions obtained in step S44 in FIG. 8 (step S45 in FIG. 8).

After that, the calculation processing section 91 judges whether or not the small region is a region showing a residue based on the color tone of the small region detected in step S45 in FIG. 8 (step S46 in FIG. 8).

Here, a specific example of the processing performed to judge whether or not the small region is a region showing a residue based on the color tone will be described.

First, the calculation processing section 91 converts RGB values of the small region detected in step S45 in FIG. 8 to chromaticity coordinates (x, y) using publicly known processing.

Next, the calculation processing section 91 judges whether or not the obtained chromaticity coordinates (x, y) satisfy the relationship in Expression (1) below in a CIExy chromaticity diagram.

(Expression 1)

$$y > \frac{(0.4 - 0.0)}{(0.6 - 0.4)}(x - 0.4) \quad (1)$$

When the obtained chromaticity coordinates (x, y) do not satisfy the relationship in Expression (1) above, the calculation processing section 91 judges that the small region detected in step S45 in FIG. 8 shows an element (blood or the like) other than the residue, and also considers it unnecessary to correct the bending target position calculated in step S42 in FIG. 8 and outputs the calculation result of the bending target position to the bending control section 5. On the other hand, when the obtained chromaticity coordinates (x, y) satisfy the relationship in Expression (1) above, the calculation processing section 91 judges that the small region detected in step S45 in FIG. 8 shows a residue, considers it necessary to correct the bending target position calculated in step S42 in FIG. 8 and continues to perform processing from step S47 in FIG. 8 onward.

After that, the calculation processing section 91 approximates the small region judged to show the residue with an ellipse (step S47 in FIG. 8).

Based on the ellipse obtained in step S47 in FIG. 8, the calculation processing section 91 calculates two tangent vectors Ve1 and Ve2, the starting point of which is the center of the original image and the end point of which is a contact in the ellipse. Furthermore, the calculation processing section 91 calculates a vector Vf, the starting point of which is a center D3 of the circle set in step S43 in FIG. 8 and the end point of which is the bending target position calculated in step S42 in FIG. 8.

Of the two tangent vectors Ve1 and Ve2, the calculation processing section 91 calculates one tangent vector having a relatively small angle formed with the vector Vf as a vector for correcting the bending target position (step S48 in FIG. 8).

The calculation processing section 91 generates a combined vector obtained by adding up the aforementioned one tangent vector (Ve1 or Ve2) and vector Vf at a third ratio and sets the pixel position which corresponds to the end point of the combined vector as a corrected bending target position (step S49 in FIG. 8). Through such processing, the bending target position calculated in step S42 in FIG. 8 is corrected to a new bending target position.

After that, the calculation processing section 91 outputs the calculation result of the corrected bending target position obtained in step S49 in FIG. 8 to the bending control section 5.

The bending control section 5 then performs control based on the processing result of the series of processes shown in FIG. 8 and can thereby bend the bending portion 16 so as to avoid contact of the distal end face of the distal end portion 15 with the residue existing in the body cavity as much as possible.

Here, as a third modification example of the present embodiment, a series of processes performed to correct the bending target position using the extraction result of the dark region in the original image and the extraction result of a gradient of pixel values in the original image will be described with reference to FIG. 9 or the like.

First, the calculation processing section 91 acquires an original image corresponding to an inputted video signal (step S61 in FIG. 9).

Next, the calculation processing section 91 extracts a dark region in the original image acquired in step S61 in FIG. 9 and then sets the center of the dark region as a bending target position of the bending portion 16 (passage target position of the distal end portion 15) using publicly known processing (step S62 in FIG. 9).

Furthermore, the calculation processing section 91 sets a circle imitating the distal end face of the distal end portion 15 in the center of the acquired original image (step S63 in FIG. 9) and then divides the portion including the interior and a boundary of the circle into a plurality of small rectangular regions (step S64 in FIG. 9). To be more specific, the circle set in step S63 in FIG. 9 is divided into a plurality of small regions as shown, for example, in FIG. 10 through the processing in step S64 in FIG. 9.

Next, the calculation processing section 91 calculates an average of pixel values in each small region obtained in step S64 in FIG. 9 (step S65 in FIG. 9).

Furthermore, the calculation processing section 91 detects a gradient direction from the bright region toward the dark region for each small region using the average of pixel values in each small region calculated through the processing in step S65 in FIG. 9 (step S66 in FIG. 9). To be more specific, the calculation processing section 91 compares the average of pixel values in one small region with averages of pixel values in eight small regions in the vicinity of the one small region respectively and detects a direction in which small regions exist whose average of pixel values is lower than the one small region out of the eight nearby small regions as the aforementioned gradient direction (for each region).

On the other hand, the calculation processing section 91 sequentially traces the gradient directions detected in step S66 in FIG. 9 and thereby acquires a route from the small region including the center of the circle set in step S63 in FIG. 9 to the small region near the boundary of the circle. The route is acquired as shown, for example, in FIG. 11.

The calculation processing section 91 then calculates a vector for correcting the bending target position Vg, the starting point of which is a center D4 of the circle set in step S63 in FIG. 9, having the same size as a radius R4 of the circle, oriented toward the same direction as the gradient direction in a small region including the start point of the route or the gradient direction in a small region including the end point of the route (step S67 in FIG. 9). Furthermore, before and after the processing in step S67 in FIG. 9, the calculation processing section 91 performs processing of calculating a vector Vh, the starting point of which is the center D4 of the circle set in step S63 in FIG. 9 and the end point of which is the bending target position calculated in step S62 in FIG. 9.

The calculation processing section 91 generates a combined vector obtained by adding up the aforementioned vectors Vg and Vh at a fourth ratio and then sets a pixel position corresponding to the end point of the combined vector as a corrected bending target position (step S68 in FIG. 9). Through such processing, the bending target position calculated in step S62 in FIG. 9 is corrected to a new bending target position.

After that, the calculation processing section 91 outputs the calculation result of the corrected bending target position obtained in step S68 in FIG. 9 to the bending control section 5.

The bending control section 5 then performs control based on the processing result of the series of processes shown in FIG. 9, and can thereby bend the bending portion 16 so as to avoid contact of the distal end face of the distal end portion 15 with the fold or body wall existing in the body cavity as much as possible.

As described above, the endoscope system 1 of the present embodiment performs a calculation using the extraction result of the dark region in the original image and image elements other than the extraction result of the dark region in the original image, and can thereby set an appropriate bending target position (passage target position) such that the distal end face of the distal end portion 15 does not contact an object existing in the insertion direction of the endoscope 2. Therefore, the endoscope system 1 of the present embodiment can insert the endoscope more smoothly than conventional ones.

On the other hand, in addition to the case where a preset one bending target position is corrected and the bending portion is bent according to another corrected bending target position, the present embodiment may also include an application example where, for example, a preset one image pickup target position is corrected and the image pickup state of the image pickup section is adjusted according to another corrected image pickup target position.

To be more specific, examples of the configuration corresponding to the aforementioned application example include a configuration where the objective optical system of the image pickup section 15a includes a zoom lens and the processor 6 includes a lens drive control section to drive the zoom lens.

Furthermore, as an operation corresponding to the aforementioned configuration, the calculation processing section 91 performs processing of setting one image pickup target position based on one piece of information (information on the dark region) obtained from the image of the object picked up by the image pickup section 15a and then calculating another image pickup target position, which is different from the one image pickup target position based on other information (information on any one of the bright region, edge, color tone and gradient of the pixel value) obtained from the image. Furthermore, following the above described processing, when the other image pickup target position is outside the image (outside the range of the observation field of view of the image pickup section 15a), the lens drive control section performs control so as to drive the zoom lens of the image pickup section 15a to the wide-angle side.

When an application example provided with the above described configuration and operation is executed, it is possible to obtain an effect of being able to insert the endoscope more smoothly than conventional ones.

The present invention is not limited to the aforementioned embodiment, but it goes without saying that the present invention can be modified or applied in various ways without departing from the spirit and scope of the invention.

What is claimed is:

1. An endoscope system comprising:
    a passage position setting section configured to:
        extract a dark region in an image picked up by an image pickup section arranged to a distal end portion of an insertion portion of an endoscope, and
        set a pixel position that is the center of the dark region as an initially-determined passage position of the distal end portion of the insertion portion of the endoscope; and
    a passage position correction section configured to:
        set a circle imitating a distal end face of the distal end portion, the circle being set in the center of the image and having a predetermined radius,
        extract a brightest region in the image and a boundary line of the brightest region,
        linearize a portion of the boundary line that is the interior of the circle,
        calculate a first vector having the center of the circle as a first vector initial point, a direction of the normal to the linearized portion of the boundary line as a first vector direction, and the radius of the circle as a first vector magnitude,
        calculate a second vector having the center of the circle as a second vector initial point, and a second vector direction and a second vector magnitude defined by the second vector initial point and the initially-determined passage position as a second vector end point, and
        set a pixel position that corresponds to an end point of a combination of the first vector and second vector as a corrected passage position of the distal end portion of the insertion section of the endoscope.

2. The endoscope system according to claim 1, further comprising an image pickup state adjusting section that adjusts an image pickup state of the image pickup section based on the information on the corrected passage position set by the passage position correction section.

3. The endoscope system according to claim 1, further comprising:
    the endoscope including:
        the insertion portion, the insertion portion including, at the distal end thereof, the distal end portion and a bending portion that bends to direct the orientation of the distal end portion, and
        the image pickup section arranged to the distal end portion of the insertion portion; and
    a bending control section that performs control to bend the bending portion to orient the distal end portion to pass through the corrected passage position set by the passage position correction section.

4. The endoscope system according to claim 1, wherein the boundary line is extracted using information on the brightest region in the image.

5. The endoscope system according to claim 1, wherein the boundary line is extracted using information on an edge of the image.

6. The endoscope system according to claim 1, wherein the boundary line is extracted using information on a color tone of the image.

7. The endoscope system according to claim 1, wherein the boundary line is extracted using any one of information on the brightest region of the image, information on an edge of the image, and information on a color tone of the image.

* * * * *